United States Patent [19]

Galusky

[11] 3,993,580
[45] Nov. 23, 1976

[54] CONTINUOUS PRODUCTION OF HYDRATED LIPIDS

[75] Inventor: Thom B. Galusky, Medina, Ohio

[73] Assignee: SCM Corporation, New York, N.Y.

[22] Filed: May 13, 1974

[21] Appl. No.: 469,104

[52] U.S. Cl. ............................... 252/311; 252/356; 426/417; 426/604; 426/653
[51] Int. Cl.² ...................... B01J 13/00; B01F 3/12
[58] Field of Search ........... 426/417, 439, 339, 602, 426/506, 603, 604, 653, 654; 252/311, 312, 356

[56] References Cited
UNITED STATES PATENTS

| | | | |
|---|---|---|---|
| 2,254,049 | 8/1941 | Schutte | 426/602 X |
| 2,422,633 | 6/1947 | Peterson | 426/339 X |
| 2,592,224 | 4/1952 | Wilson et al. | 426/339 X |
| 2,797,164 | 6/1957 | McGowan | 426/339 |
| 2,871,125 | 1/1959 | Kuhrt | 426/24 |
| 2,997,396 | 8/1961 | North | 426/339 X |
| 3,033,689 | 5/1962 | Elwood et al. | 426/339 X |
| 3,379,535 | 4/1968 | Landfried et al. | 426/417 X |
| 3,533,802 | 10/1970 | Cooper et al. | 426/602 X |
| 3,702,307 | 11/1972 | Norris | 426/226 |

FOREIGN PATENTS OR APPLICATIONS

| | | | |
|---|---|---|---|
| 1,066,406 | 2/1955 | Germany | 426/339 |
| 1,130,268 | 1/1954 | Germany | 426/339 |
| 736,710 | 9/1955 | United Kingdom | 426/339 |

*Primary Examiner*—Frank W. Lutter
*Assistant Examiner*—N. Greenblum
*Attorney, Agent, or Firm*—Merton H. Douthitt; Jerry K. Mueller, Jr.

[57] ABSTRACT

Efficient production of high-quality hydrated products from hydratable lipid particulates such as partial glyceride particulates has been obtained continuously. A flow sequence of controlled heating and cooling with intermediate application of smoothing shear stress is involved.

3 Claims, 1 Drawing Figure

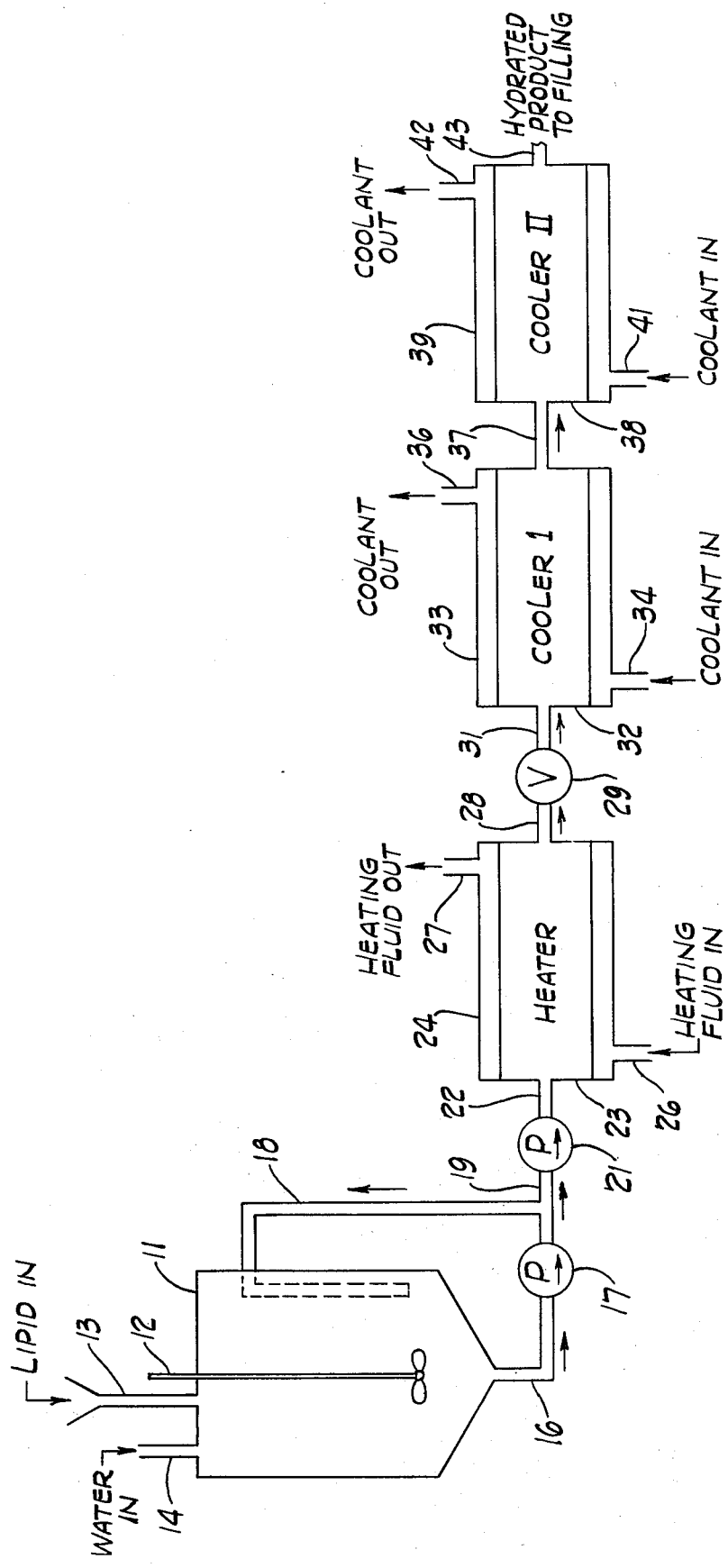

CONTINUOUS PRODUCTION OF HYDRATED LIPIDS

This application relates to a process for the continuous production of hydrated lipids of plastic consistency such as hydrated food emulsifiers from particulates of same. Often such hydrated emulsifiers contain a substantial proportion of triglyceride fats having saturated and frequently some unsaturated fat-forming acids of $C_{2-26}$ carbon atoms.

Heretofore it has been conventional industrial practice to make such hydrated products by a batch process. The batch process comprises mechanically agitating the lipid such as a monoglyceride of a higher fatty acid with all or part of the water for the hydrated product at an elevated temperature, e.g. 150°–180°F. or even higher. As such lipid begins to hydrate, the viscosity of the resulting mixture increases. The fluid usually goes from one having Newtonian flow characteristics to one distinctly non-Newtonian. This makes for increasingly inefficient mixing, particularly in a large batch. Accordingly, even with prolonged mixing, incompletely hydrated and/or non-homogeneouly hydrated products often are produced.

Lipids that are hydrated generally include partial glycerides of higher ($C_{12-26}$) fatty acids, i.e., monoglycerides and diglycerides and particularly those from 0 to about 70 I.V., in varying concentrations from about 10% to all or virtually all of the total lipid. Other lipoidal emulsifiers useful for making the instant hydrates include acetoglycerides, glycerol mixed esters of water soluble hydroxy carboxylic and higher fatty acids, higher fatty acid esters of lactylic acids, sorbitan esters of higher fatty acids, polyoxyalkylene derivatives of sorbitan esters of higher fatty acids, glycol esters of higher fatty acids and their polyoxyalkylene derivatives, higher fatty acid esters of polyglycerols and their polyoxyalkylene derivatives, tartaric acid esters of higher fatty acid monoglycerides, stearyl monoglyceridyl citrate, higher fatty acid esters of citric acid such as dipalmityl or distearyl citrate, sucrose esters of higher fatty acids, alkoxylated partial higher fatty esters of polyhydric alcohols having from 2 to 6 carbon atoms, various mixtures of these with each other, and especially with partial glycerides. The resulting hydrated product is useful in the preparation of foods, cosmetics, and pharmaceuticals if made of materials appropriate for such use.

My optimally hydrated lipid product is smooth, having a fat plus emulsifier (lipid) phase in its most stable crystalline form, and having a thermal stability test approximately equal to the C.M.P. of the fat and emulsifier blend.

Such emulsifier or mixture of emulsifiers for hydration often includes indigenously from its commercial manufacture or is deliberately blended with a significant proportion of edible triglycerides of fatty acids having $C_{2-26}$ and more generally $C_{12-26}$ carbon atoms, such fats generally being solid or plastic with I.V. from 0 to about 110. The proportion of such triglyceride can be from a few percent up to as much as 60–80% of the total lipid content of the resulting hydrated product. Such product also can contain small proportions of other edible ingredients which do not detract from its stability and utility, e.g., various edible gums such as gum tragacanth or algin derivatives, antifoaming and antispattering agents, food colors, lactic, phosphoric, and acetic acids, antioxidants and other preservatives such as propionic acid, benzoic acid, sorbic acid, salts of these, or BHA or BHT, lecithin and lecithin derivatives, synthetic and natural sweeteners, etc. U.S. Pat. Nos. showing the preparation of hydratable lipids into hydrated form include 3,702,307; 2,380,166, and 2,508,393.

My improvement in process for production of hydrated product from hydratable lipid comprises: forming a suspension in water of said lipid in discrete particulate form; passing an input stream of said suspension continuously into a swept-surface, indirect heater; therein heating said input stream to pumpable hydration temperature while mechanically working said stream into a plastic mass; continuously withdrawing an exit stream of resulting plastic mass from said heater; subjecting the withdrawn exit stream to shear stress sufficient for increasing its smoothness; continuously passing the resulting smoothed, withdrawn exit stream into a swept-surface, indirect cooler; therein cooling the said smoothed stream to a stabilizing, yet pumpable temperature; and continuously withdrawing the resulting cooled, smoothed stream from said cooler.

The DRAWING is a flow diagram of my process being operated to produce continuously a typical hydrated, food grade emulsifier product which is by weight 75% water and 25% distilled hard-based monoglyceride (Myverol 1800—a trademark of the Eastman Kodak Company) having the following specification: $\alpha$-monoglyceride, 90% minimum; total monoglycerides of $C_{14-22}$ fatty acids of 95%; Iodine Value below 2; Lovibond color of 2 red and 10 yellow maximum, free fatty acid of 0.6% maximum; and capillary melting point of 154°–156° F.

The apparatus in contact with the edible fatty substance is of austenitic stainless steel. Shutoff valves, drains, sample points, instrumentation, and other auxiliary appurtenant equipment are not shown, but are to be provided for conventionally as necessary or desirable.

Tank 11 is an atmospheric blending tank equipped with agitator 12 and an indirect heater not shown. Beads of this monoglyceride (average particle size of 350–500 microns) are charged into inlet 13, and water into inlet 14 in the 25/75 proportion. In the tank the particles are suspended in the water by mechanical agitation. The resulting suspension is warmed to 90°–120° F. Little or no hydration takes place. A stream of such suspension is withdrawn through outlet 16 and passed by centrifugal pump 17 into inlet line 19 of positive displacement pump 21 (a gear pump). The balance of the discharge of pump 17 returns through line 18 into tank 11. The stream of suspension discharges from positive displacement pump 21, flows through line 22, then into swept-surface, indirect heater 23.

Heater 23 is a Crepacko (a trademark of the Creamery Packaging Company) swept-surface heat exchanger of concentric rotor design. It has a mechanically-scraped inner wall and is jacketed with heat exchange jacket 24. Saturated steam at 110 psig enters jacket inlet 26, and is trapped by means not shown, then exits as condensate from jacket outlet 27.

In heater 23 the temperature must be raised to a temperature which will make a pumpable hydrate ("pumpable hydration temperature"). For this particular hydrate it is 160°–165° F. The hydrate exit flow temperature from heater 23 can be controlled to about ± 1° F. The monoglyceride-bearing stream hydrates quickly during an average residence time in heater 23 between about 30 seconds and about 1 minute.

The resulting output of plastic mass then flows through line 28 into low-pressure, adiabatic, homogenizing valve (pressure drop of 500 psi). This applies sufficient shear stress to increase the smoothness of the flowing hydrate. (In some cases the hydration, which is done mainly in heater 23, can be finished by such shear stressing and/or the lipid can be directed to the most desirable crystal form for use, e.g., predominantly β-crystalline).

The thus-homogenized flow continues through line 31 into cooler 32, line 37, and cooler 38. These coolers are of the same style as the heater, except that their jackets 33 and 39, respectively are charged with coolants. Cooler 32 is jacketed with jacket 33 having coolant inlet 34 and coolant outlet 36. In the first cooler 32 the coolant is chilled water (40°–75° F.). Cooler 38 is jacketed with jacket 39 having coolant inlet 41 and coolant outlet 42. In the second cooler 38 the coolant is evaporating Freon R12 (halogenated alkane—a trademark of E. I. duPont de Nemours and Company) at 15–20 psig gas outlet back pressure. In such cooler the product flow is cooled to 70°–100° F. outlet temperature. Then it passes through outlet 43 as finished hydrated product to a station (not shown) for filling into drums or other conventional packages.

The hydrate of a particular lipid or lipid mixture can have water content from roughly 20% to 80% based on total mass of hydrate product. A fraction of the necessary hydration water can be added into the process, as, for example, at inlet line 19 to positive displacement pump 21 in order to cut down on the size of tank 11, and such water can be prewarmed to approach hydration temperature for reducing the heat load on heater 23.

Optimum hydration temperature or temperature range and optimum hydration time should be determined for each kind of hydrated lipid or lipid mixture being made. Generally such temperature will be between 130° and 180° F., but within that range small differences in temperature can be significant. If the hydration temperature is too high, hydration occurs extremely quickly and a highly viscous, virtually unpumpable hydrate gel can be formed. If the hydration temperature is too low, the hydration does not occur rapidly or completely enough, and substantial underhydrated (free water remains in the heater output and/or syneresis of the hydrate occurs when the product is gently heated) or unhydrated lipid remains in an otherwise somewhat hydrated product. Hence, by practical pumpable hydration temperature, I mean a temperature in the range where the product is completely or substantially completely hydrated while readily pumpable at a pressure no greater than about 1000 psig through 25 feet of Schedule 40, 3" standard pipe by a conventional positive displacement pump. The viscosity of said product rarely will exceed 2000–3000 centipoises at room temperature and at 10,000 centipoises these hydrates are virtually unpumpable. Within its broad temperature range for possible hydration the pumpable hydration temperature range can be as little as 6° to 8° F. between upper and lower limits. Hydration times can be from about 10 sec. to about 5 min. at the optimum hydration temperature. Generally at least 30 seconds and not more than about one minute are preferred in heater 23 to achieve good hydration and efficiency.

Preferably the feed to the mixer for forming the initial suspension desirably is as warm as possible while maintaining substantially all of the normally solid or plastic lipid present in discrete particulate form. Generally 90°–120° F. is as high as one can go in such mixing operation, at which temperature little or no hydration occurs and the viscosity of the mixture usually is like that of water. With some of the "softer" emulsifiers or other lipids even lower temperatures are advantageous to preclude substantial hydration at this stage. It is advantageous also to compound normally very soft or sticky lipids so that they are preblended into or occluded by, or otherwise incorporated into the matrix of normally harder lipids for hydration. The preferred lipid feed is one melted (in precise proportions of the various component lipids if a blend of lipids is to be hydrated), then spray chilled into discrete beads of substantially spheroidal conformation having average diameter between about 120 and about 550 microns.

Alternatively such molten material can be flaked into small flakes on a chilled roll; the flakes even can be further subdivided by grinding (although this is less advantageous and occasionally difficult because of the heat of grinding). For best performance in my process the hard or plastic lipid particles should have their greatest dimension no larger than about 800 $\mu$, and preferably should be between 100 and 500 $\mu$ average particle size. Frequently the lipid particles for hydration can be a mechanical blend of two or more particulate lipids. It is possible, also, to add a flowable (under pressure) ostensibly amorphous or liquid lipid to the suspension prior to its hydration along with normally hard or plastic lipids. This advantageously can be done by metering the amorphous material into tank 11 or into the inlet of pump 21 in controlled proportion (by itself or admixture with an oily, fatty edible material).

The swept (or scraped) surface heat exchangers used in this process can be heated and cooled in various conventional indirect ways. Useful heating fluids include steam, water, oil, and glycol. Useful cooling fluids include water, ammonia, and other conventional refrigerants. Where heat exchangers are put in parallel for a single step, the same heat exchange medium is best used in all of them, but where they are put in series for a single step, it is sometimes advantageous to use diverse heat exchange mediums in the heat exchange stages.

While it is preferred to use a low-pressure homogenizing valve 29 as shown in the drawing, this can be replaced by a high shear, totally enclosed, mechanically-driven blender such as a Gifford-Wood Company pipeline mixer, or a high shear in-line mixer such as a Line Blender mixer (a trademark of Mixing Equipment Company). Other useful high-shear apparatus for this operation includes: a Cowles Dissolver (a trademark of Morehouse-Cowles Company); a Dispersator (a trademark of Premier Mill Company); and an E. T. Oakes Corporation mixer. A simple test for an adequate shearing operation in my process is to press a sample of valve 29 output between thumb and forefinger; if no "grit" is felt, the product is acceptable. Alternatively, one can use a Hegmann gauge (e.g. No. 8) to discern grit visually (palpable hard gel particles).

The following example shows how my process has been used on a pilot scale and is described with reference to the drawing. This example should not be construed as limiting the invention. In this specification, all parts are parts by weight, all percentages are weight percentages, and all temperatures are in degrees Fahrenheit unless otherwise expressly indicated.

EXAMPLE

Referring to the drawings 75 parts of deionized, potable water and 25 parts of Myverol 1800 brand monoglyceride were charged into tank 11. The contents were agitated to establish and maintain suspension. The monoglyceride was in the form of beads having 420 microns average particle size. In the tank the suspension was heated indirectly to 90° F., then circulated from the bottom of the tank by pump 17 and line 18 at a rate of approximately 20 gpm for the duration of the run to maintain homogeneity of the suspension. From this circulating stream pump 21 pumped the suspension into heater 23, through valve 29, then through coolers 32 and 39 and outlet 43 to yield 200 pounds per hour of hydrated product continuously.

This product was smooth (without any palpable lumps) and homogeneous, with no evidence of under- or over-hydration, it was in condition for direct filling into finished goods containers. Its thermal stability was excellent, such point being 162°. It was useful as a food emulsifier in cakes, breads and other bakery products.

Pressures in this flow process were as follows: pump 21 discharge, 610 psig; heater 23 discharge, 600 psig; valve 29 discharge, 100 psig; outlet 43 was to atmosphere. Temperatures in the process were as follows: suction to pump 21, 90°; discharge from heater 23, 165°; discharge from cooler 39, 80°. Heater 23 was a laboratory size Crepacko Model No. 3-BD-620-S swept surface heat exchanger having approximately 30 seconds holding time at the throughput. Coolers 32 and 38 were a pair of like exchangers in series and had a total residence time of approximately 60 seconds at the throughput. The heating fluid in heater 23 was saturated steam at 110 psig. Steam in jacket 24 of heater 23 was trapped by a conventional steam trap and discharged as hot condensate. The cooling fluid in cooler 32 was water in at 55° and out at 75 °. Cooler 38 used Freon R12 as described above. The homogenizing valve was a Crepacko aseptic, remote, single-stage unit Model No. CTA-40.

Thermal stability is determined by monitoring the phase changes occuring during the melting transistion of a hydrate sample utilizing a polarized-light microscope. The apparatus consists of a microscope coupled with a conventional hot stage and sample holder assembly with thermometers connected to a calibrated resistance (wheatstone bridge), a 110 volt rheostat for regulating the power output from a 110 volt constant voltage transformer in line with a 110 volt A.C. supply as the power source, microscope slides and a cooling block. The sample is loaded onto the slide, accommodated on the hot stage assembly, heated at 1°-2° C/minute and observed under polarized light at 100 to 200x. The temperature at which the gel-phase disappears completely is recorded as the approximate phase change melting point.

The hot stage assembly is cooled approximately 5° C below the approximate phase change melting point, a new sample slide loaded and heated at 0.5° C/minute. The temperatures are recorded at which the outset of water loss occurs, 50% of the hydrate remains, less than 10% of the hydrate remains, and total disappearance of the hydrate. The temperature at which the total hydrate disappears is known as the phase change melting point or thermal stability point of the hydrate.

As noted in the above example, the hydrated product emerging from outlet 43 was in condition for direct filling into containers at 80°, this being well below thermal stability point of the hydrate. While a stabilizing temperature for cooling and storing hydrate can be anything below such thermal stability point, it usually is at least about 10° below same and ordinarily in the range of 50°–100° F. (to maintain pumpability of the product with a conventional positive displacement pump). Cooling to below the dew point of the ambient atmosphere is usually unnecessary and naturally undesirable for efficiency and economy. Additional pumping means, of course, can be utilized between the various processing steps or stages but, as demonstrated in the foregoing example, are not usual.

For the purposes of this specification a normally solid lipid or mixture of lipids is one that at 115° F. is dry to touch, free-flowing in small beaded form, which beads do not tend to agglomerate strongly or appreciably or to deform appreciably, even when standing unpacked to a depth of 6″ high in a 1″ diameter cylinder for 24 hours at 70°–80°. A normally plastic counterpart at 100° F. usually is greasy to touch, tends to agglomerate at points of contact in small beaded form, and will deform appreciably on like standing for 24 hours, but will not thereby lose much of its generally particulate identity by such flow or by coalescence. Sticky, usually amorphous, lipids usually have appreciable plastic or fluid flow at 70° F., and cannot be beaded readily by themselves at temperature as low as 40° F. Normally liquid lipids are those having a liquid continuous phase or are entirely liquid at 50° F. Sticky amorphous and normally liquid lipids are best thoroughly intermixed in a matrix of normally solid ones for ease of handling in this process; such mixture can assume a plastic or plasticized character, but yet be quite useful in this process.

I claim;
1. A process for the production of hydrated product from hydratable lipid particulates which comprises:
    forming a suspension in water of said particulates at a temperature where substantially no hydration of said lipid particulates occurs;
    passing an input stream of said suspension continuously into a swept-surface, indirect heater;
    therein heating said input stream to pumpable hydration temperature while mechanically working said stream into a plastic mass;
    continuously withdrawing an exit stream of resulting plastic mass from said heater;
    subjecting the withdrawn exit stream to shear stress sufficient for increasing its smoothness;
    continuously passing the resulting smoothed, withdrawn exit stream into a swept-surface, indirect cooler;
    therein cooling said smoothed stream to a stabilizing, yet pumpable temperature; and
    continuously withdrawing the resulting cooled, smoothed stream from said cooler.
2. The process of claim 1 wherein said lipid comprises an edible emulsifier.
3. The process of claim 2 wherein said lipid includes a substantial proportion of edible triglyceride fat.

* * * * *